(12) United States Patent
Fakhfakh et al.

(10) Patent No.: US 7,342,026 B2
(45) Date of Patent: Mar. 11, 2008

(54) SUBSTITUTED QUINOLINES FOR THE TREATMENT OF PROTOZOA AND RETROVIRUS CO-INFECTIONS

(75) Inventors: Mohamed Fakhfakh, Chatenay-Malabry (FR); Bruno Figadere, Saint-Cheron (FR); Alain Fournet, Ossages (FR); Xavier Franck, Chevilly-Larue (FR); Reynald Hocquemiller, Limours (FR); Eric Prina, Les-Clayes-Sous-Bois (FR)

(73) Assignees: Institut de Recherche pour le Developpement, Paris (FR); Centre National de la Recherche Scientifique, Paris (FR)

( * ) Notice: Subject to any disclaimer, the term of this patent is extended or adjusted under 35 U.S.C. 154(b) by 759 days.

(21) Appl. No.: 10/466,566

(22) PCT Filed: Jan. 15, 2002

(86) PCT No.: PCT/FR02/00140

§ 371 (c)(1),
(2), (4) Date: Jul. 29, 2003

(87) PCT Pub. No.: WO02/057238

PCT Pub. Date: Jul. 25, 2002

(65) Prior Publication Data

US 2005/0165052 A1   Jul. 28, 2005

(30) Foreign Application Priority Data

Jan. 17, 2001   (FR) .................................. 01/00580

(51) Int. Cl.
*A61K 31/47* (2006.01)
*C07D 215/38* (2006.01)
*C07D 215/44* (2006.01)

(52) U.S. Cl. .............. 514/312; 514/311; 514/314; 514/313; 546/153; 546/159; 546/171

(58) Field of Classification Search .............. 514/312, 514/313, 314, 311; 546/153, 159, 171
See application file for complete search history.

(56) References Cited

U.S. PATENT DOCUMENTS

| 3,488,728 | A | * | 1/1970 | Eichenberger et al. ...... 544/238 |
| 5,153,202 | A | * | 10/1992 | Davis ............................ 514/311 |
| 5,278,173 | A | * | 1/1994 | Davis ............................ 514/312 |
| 6,025,390 | A | | 2/2000 | Farina et al. |

FOREIGN PATENT DOCUMENTS

| EP | 0 305 968 | * | 3/1989 |
| FR | 2 761 687 A1 | | 10/1988 |
| WO | WO 93/07125 | | 4/1993 |
| WO | 00/44387 | * | 8/2000 |
| WO | 01/12155 | * | 2/2001 |
| WO | 01/16357 | * | 3/2001 |

OTHER PUBLICATIONS

Manning, CA 46:30931, abstract of Australasian J Pharm, vol. 31, pp. 764-766, 1951.*
Potts, CA 38:16662, abstract of Journal of the Franklin Institute, vol. 237, pp. 227-231, 1944.*
Queener, Antimicrobial Agents and Chemotherapy, vol. 37, No. 10, pp. 2166-2172, 1993.*
Tojo, J of Fish Diseases, vol. 17(2), pp. 135-143, 1994.*
Ouali, J Med Chem, vol. 43, pp. 1949-1957, 2000.*
International Search Report.
Fournet, A., et al.; The activity of 2-substituted quinoline alkaloids in BALB/c mice infected with *Leishmania donovani, Chemical Abstracts*, vol. 121, No. 7, Abstract No. 73107s (Aug. 15, 1994).
Mohamed A. Fakhfakh et al. Expeditious preparation of 2-substituted quinolines, *Tetrahedron Letters*, vol. 42, No. 23, pp. 3847-3850 (Jun. 4, 2001).
Austin et al., "$S_{RN}1$ Reactions of aryl halides with carbanions initiated by sodium amalgam in liquid ammonia", *Tetrahedron*, vol. 49, No. 21, pp. 4495-4502, 1993.

* cited by examiner

Primary Examiner—D. Margaret Seaman
(74) Attorney, Agent, or Firm—Alston & Bird LLP

(57) ABSTRACT

The invention relates to the use of quinolines having general formula (I), wherein $R_1$ denotes H; alkyl $C_1$-$C_{15}$; alkenyl or alkynyl $C_2$-$C_{15}$; —CHO; heteroaryl; alkyl $C_1$-$C_{15}$ or alkenyl or alkynyl $C_2$-$C_7$ comprising at least one substituent selected from among O, halogen, —OH, —CHO, —COOH, aryloxycarbonyl, alkyloxycarbonyl $C_2$-$C_8$, alkenyloxycarbonyl $C_3$-$C_9$, nitrile, aryl, heteroaryl, arylsulphone, alkylsulphone $C_1$-$C_7$, thioalkyl or aminoalkyl $C_1$-$C_7$; alkenyl $C_2$-$C_7$ bearing at least one substituent selected from among $NH_2$, aleoxy $C_1$-$C_7$, phenoxy, cycloakyl $C_3$-$C_6$ or heteroaryloxy, alkenyl or alkynyl $C_2$-$C_{15}$ comprising at least one trialkylsilyl $C_1$-$C_7$; $R_2$, in position 3, 6 or 8, denotes H; halogen; —OH; —CHO; —COOH; alkyl or aleoxy $C_1$-$C_7$; —NH2; alkenyl $C_2$-$C_7$; or alkynyl $C_2$-$C_{10}$; $R_1$ and $R_2$ do not both denote H. The invention is used for the preparation of a medicine to treat protozoan and retrovirus co-infections (I)

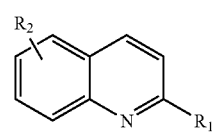

16 Claims, 1 Drawing Sheet

Figure 1:
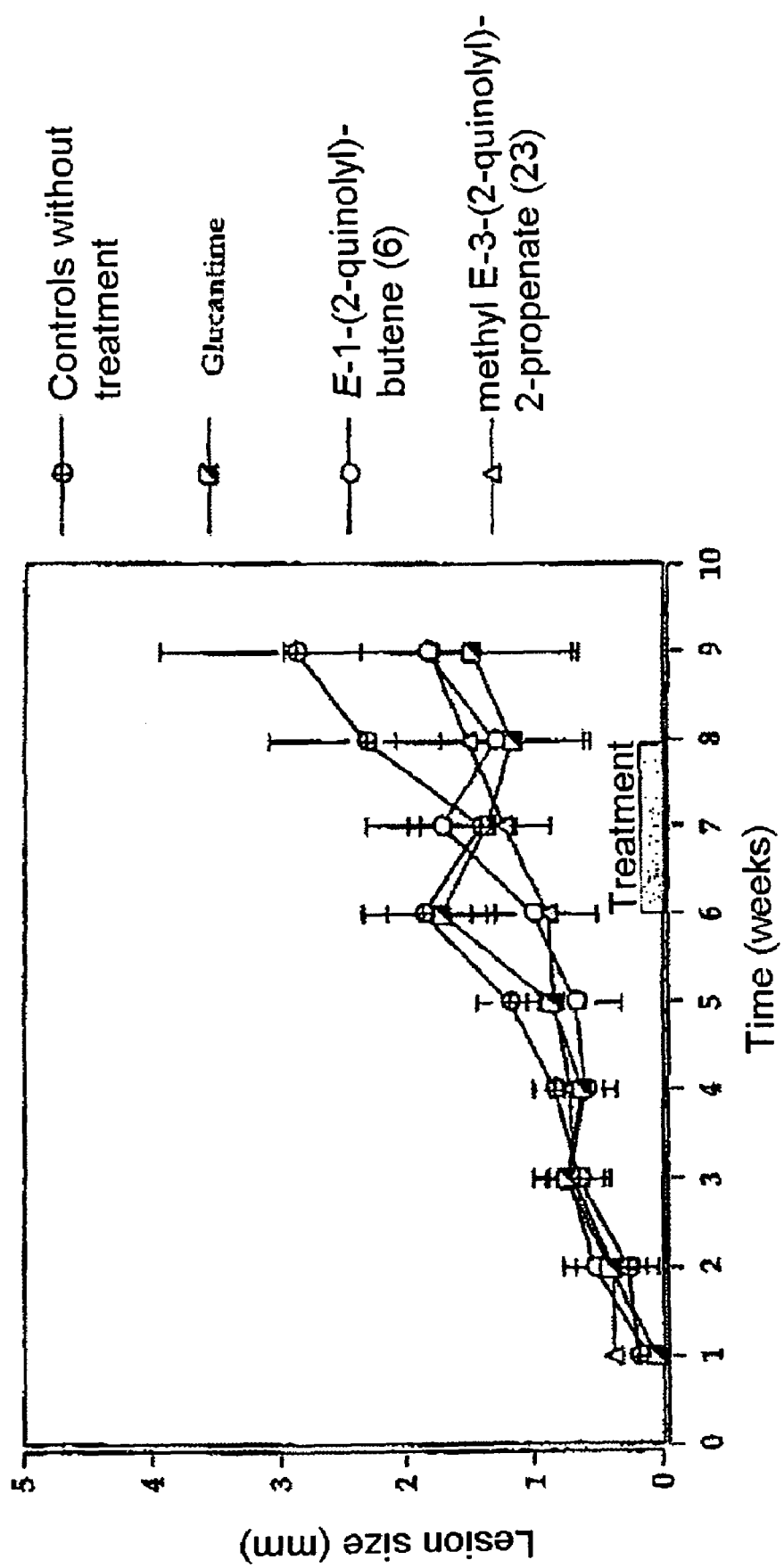

SUBSTITUTED QUINOLINES FOR THE TREATMENT OF PROTOZOA AND RETROVIRUS CO-INFECTIONS

The invention relates to substituted quinolines for the treatment of protozoan and retrovirus co-infections.

The geographical regions endemic for diseases due to protozoa (leishmaniasis, trypanosomiasis, malaria, etc.) are also zones where retroviral diseases, and in particular acquired immunodeficiency syndrome, or AIDS, are highly prevalent.

As a result, for several years, the emergence of protozoan and retrovirus co-infections of the Leishmania/HIV-1, Plasmodium/HIV or else Pneumocystis carinii/HIV type has been witnessed, the number of which is continually increasing, and which are extremely serious and greatly reduce the life expectancy of the individuals suffering from them.

Thus, for example, visceral leishmaniasis, or kala-azar, which is induced by Leishmania donovani and Leishmania infantum and which represents the most severe form of leishmaniasis, is considered to be a particularly exacerbating factor in the evolution of AIDS (WHO, 1997, Weekly Epidemiol. Rec., 72: 49-54).

It is known that some protozoa, such as leishmania, trypanosomes and toxoplasms, and HIV have the ability to infect and to multiply in specific host cells such as macrophages, monocytes and dendritic cells, which play a primordial role in the setting up and developing of immune responses against pathogenic agents.

It is also known that the consequence of co-infection of these cells with different pathogenic agents is to increase the weakening of the immune system and to promote the multiplication and dissemination of these pathogenic agents in the organism (Wolday et al., Parasitology Today, 1999, 15: 182-187).

Thus, for example, studies carried out in vitro on cells of monocytic origin have shown that the presence of leishmania in this type of cell can, when said cells are subsequently infected with HIV, induce and activate replication of the latter (Bernier et al., J. Virol. 69: 7282-7275). On the other hand, the presence of HIV is capable of increasing the intracellular growth of leishmania when the cells are secondarily infected with these protozoa (Wolday et al., 1998, Scand. J. Infect. Dis., 30: 29-34). Moreover, a large percentage of patients exhibiting a Leishmania/HIV co-infection show high multiplication and dissemination of the leishmania. The immunopathological mechanisms by which the leishmania and the HIV interact on the immune system and mutually reinforce one another have not yet been elucidated. Many hypotheses have been put forward, but none of them has been really confirmed to date (Wolday et al., 1999, ibid).

Protozoan and retrovirus co-infections pose particular difficulties in terms of therapy.

Taking the case of Leishmania/HIV co-infections as an example, the anti-leishmania treatments are not always effective and failures and relapses related to phenomena of resistance or toxicity of the products are common. Thus, a study carried out in South-West Europe has shown that 52% of patients carrying a Leishmania/HIV co-infection and treated with pentavalent antimonials such as meglumine antimoniate (Glucantime®)—which represents the front-line treatment for leishmaniasis—experience one to four relapses within a period of one month to three years (WHO source).

In addition, all the anti-leishmania drugs available to date (meglumine antimoniate, pentamidine, amphotericin B) must be administered parenterally, which makes their use expensive, relatively incompatible with a lack of hospital structures and, therefore, quite often inaccessible to most of the populations of the regions affected by Leishmania/HIV co-infections.

As regards antiretroviral treatment, while it is unquestionable that its administration in tritherapy (combination of two reverse transcriptase inhibitors and one HIV protease inhibitor) improves the prognosis for Leishmania/HIV co-infections, it is known that they induce viral mutations which are responsible for the appearance of resistances and, in the end, a phenomenon of evasion of the therapy causing the infection to take hold again. In addition, since most commonly the induced resistances cross-react between various antiretroviral agents, in particular between protease inhibitors, therapeutic substitutions are very restricted. Moreover, the use of tritherapy has the major drawback of being very expensive and of itself also being inaccessible to the majority of the populations of the regions affected by Leishmania/HIV co-infections.

In PCT International Application WO 93/07125, the inventors have demonstrated that quinolines substituted on the carbon atom located in the 2-position of the quinoline ring, with an n-propyl, hydroxypropyl, n-propenyl, trans-epoxypropyl or styryl group, are active both on leishmania responsible for cutaneous and cutaneous/mucosal leishmaniasis (Leishmania amazonensis, Leishmania venezuelensis, etc.) and on those responsible for visceral leishmaniasis, when they are administered to mice, even orally.

Moreover, MEKOUAR et al. have shown, in PCT International Application WO 98/45269 and also in an article published in Journal of Medicinal Chemistry (2000, 43: 1533-1540), that 2-styrylquinolines are capable of inhibiting HIV integrase in vitro and replication of this virus in pre-infected cells of a lymphocyte line (CEM).

These authors indicated in their article, however, that the inhibiting activity of substituted quinolines with respect to HIV integrase requires not only the presence of an ancillary aromatic ring—which is represented in case in point by the phenyl group of the styryl radical—but also that of a carboxyl group and of a hydroxyl group respectively C-7 and C-8 of the quinoline ring. As regards the inhibitory activity on the intracellular replication of HIV, this would require the additional presence of a pair of substituents, located in the ortho position, and the ancillary aromatic ring, namely a C-3' hydroxyl or methoxy group and a C-4' hydroxyl group.

Now, in continuing their studies on substituted quinolines, the inventors have noted that, surprisingly, some of these quinolines, although not satisfying the structural criteria stated by the preceding authors, exhibit both antiprotozoan activity and an ability to inhibit the intracellular replication of retroviruses, and in particular of HIV, and are consequently suitable for constituting a therapy of choice for protozoan and retrovirus co-infections.

The subject of the present invention is therefore the use of at least one quinoline corresponding to general formula (I):

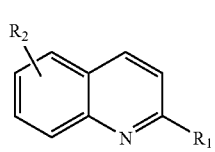

in which:
R$_1$ represents:
a hydrogen atom, a C$_1$-C$_{15}$ alkyl group, a C$_2$-C$_{15}$ alkenyl group, a C$_2$-C$_{15}$ alkynyl group, a formyl group or a heteroaryl group, the latter being optionally substituted with one or more hydroxyl groups; or else a C$_1$-C$_{15}$ alkyl or C$_2$-C$_7$ alkenyl group carrying at least one substituent chosen from oxygen, halogens, and hydroxyl, formyl, carboxyl, aryloxycarbonyl, C$_2$-C$_8$ alkyloxycarbonyl, C$_3$-C$_9$ alkenyloxycarbonyl, nitrile, amine, C$_1$-C$_7$ alkoxy, phenoxy, C$_3$-C$_6$ cycloalkyl, aryl, heteroaryl, heteroaryloxy, arylsulfone, C$_1$-C$_7$ alkylsulfone, C$_1$-C$_7$ thioalkyl and C$_1$-C$_7$ aminoalkyl groups; or else a C$_2$-C$_7$ alkynyl group carrying at least one substituent chosen from oxygen, halogens, and hydroxyl, formyl, carboxyl, aryloxycarbonyl, C$_2$-C$_8$ alkyloxycarbonyl, C$_3$-C$_9$ alkenyloxycarbonyl, nitrile, aryl, heteroaryl, arylsulfone, C$_1$-C$_7$ alkylsulfone, C$_1$-C$_7$ thioalkyl and C$_1$-C$_7$ aminoalkyl groups; or else a C$_2$-C$_{15}$ alkenyl or alkynyl group substituted with at least one C$_1$-C$_7$ trialkylsilyl group; while R$_2$, which may be in the 3-, 6- or 8-position of the quinoline ring, represents a hydrogen or halogen atom, a hydroxyl group, formyl group, carboxyl group, C$_1$-C$_7$ alkyl group, C$_1$-C$_7$ alkoxy group, amine group, C$_1$-C$_{10}$ alkylamide group or C$_2$-C$_7$ alkenyl group optionally substituted with one or more C$_1$-C$_7$ alkoxy groups, or else a C$_2$-C$_{10}$ alkynyl group, the latter being optionally substituted with a heteroaryl group;

or one of its pharmaceutically acceptable salts, on the condition, however, that R$_1$ and R$_2$ are not both a hydrogen atom, for preparing a medicinal product for treating protozoan and retrovirus co-infections.

In accordance with the invention, in general formula (I), the alkyl, alkoxy, alkenyl and alkynyl groups can be both branched and linear. The terms "aryl" and "aryl-" denote any cyclic or polycyclic radical which is aromatic in nature, while the terms "heteroaryl" and "heteroaryl-" denote any cyclic or polycyclic radical which is aromatic in nature and in which the ring(s) comprise(s) one or more atoms chosen from nitrogen, oxygen and sulfur. Moreover, the quinolines of the general formula (I) can be used in their various stereoisomer forms.

Among the quinolines of general formula (I), use is preferably made of those in which the carbon atom located in the 2-position of the quinoline ring is substituted, i.e. those in which R$_1$ is different than a hydrogen atom.

Preferably, the quinoline(s) is (are) chosen from quinolines in which the carbon atom located in the 2-position of the quinoline ring is substituted with an unsaturated hydrocarbon-based chain, i.e. an alkenyl or alkynyl group which may or may not be carrying substituents, and more particularly, from those in which:

R$_1$ represents:
a C$_2$-C$_{15}$ alkenyl or alkynyl group; or else
a C$_2$-C$_7$ alkenyl group carrying at least one substituent chosen from oxygen, halogens, and hydroxyl, formyl, carboxyl, C$_2$-C$_8$ alkyloxycarbonyl, nitrile, amine, C$_1$-C$_7$ alkoxy, phenoxy, C$_3$-C$_6$ cycloalkyl, aryl, heteroaryl, heteroaryloxy, arylsulfone, C$_1$-C$_7$ alkylsulfone, C$_1$-C$_7$ thioalkyl, C$_1$-C$_7$ aminoalkyl and trialkylsilyl, in particular trimethylsilyl, groups; or else
a C$_2$-C$_7$ alkynyl group carrying at least one substituent chosen from oxygen, halogens, and hydroxyl, formyl, carboxyl, C$_2$-C$_8$ alkyloxycarbonyl, nitrile, aryl, heteroaryl, arylsulfone, C$_1$-C$_7$ alkylsulfone, C$_1$-C$_7$ thioalkyl, C$_1$-C$_7$ aminoalkyl and trialkylsilyl, in particular trimethylsilyl, groups; while
R$_2$ represents a hydrogen atom, a hydroxyl group or a C$_1$-C$_7$ alkyl group Particularly preferably, the quinoline(s) is (are) chosen from quinolines of general formula (I) in which R$_1$ represents a C$_2$-C$_7$ alkenyl or alkynyl group substituted with one or more halogen atoms, in particular chlorine, bromine or fluorine atoms, the inventors having in fact noticed that the presence of such atoms generally results in particularly pronounced antiprotozoan properties.

All the quinolines of formula (I) can be prepared by chemical synthesis, in particular according to the processes described by Webb, *Tetrahedron Lett.*, 1985, 26, 3191-3194, Fakhfakh et al., *Tetrahedron Lett.*, 2001, 42, 3847-3850 and Fakhfakh et al., *J. Organomet. Chem.*, 2001, 624, 131-135.

The use of the quinolines of general formula (I) for preparing a medicinal product for treating protozoan and retrovirus co-infections has many advantages. Specifically, by virtue of the antiprotozoan and antiretroviral double activity of these quinolines, it makes it possible to treat the two infections with a single medication, which greatly promotes adherence to the treatment and considerably reduces the risks of drug interactions. Moreover, although their mechanism of action on HIV replication has not yet been elucidated, the quinolines of general formula (I) appear to act neither on reverse transcriptase nor on viral protease, such that their use should make it possible to avoid problems of cross-resistance with which clinicians are currently confronted in treating HIV infection. In addition, these quinolines exhibit a lack of toxicity, which pleads in favor of very satisfactory tolerance.

By way of examples of co-infections which can be treated with a medicinal product prepared in accordance with the invention, mention may be made, without this being in any way limiting in nature, of co-infections induced by one or more protozoa belonging to the *Leishmania, Trypanosoma, Plasmodium, Toxoplasma, Pneumocystis* and *Schistosomia* genera and by a retrovirus of the HIV or HTLV-1 type.

Preferably, the medicinal product is intended to treat a *Leishmania*/HIV co-infection.

The invention encompasses, for the use for preparing a medicinal product intended to treat protozoan and retrovirus co-infections, both quinolines which have already been described as being capable of having a therapeutic application and quinolines which have never been proposed as medicinal products.

A subject of the invention is therefore also a quinoline corresponding to general formula (I) represented above, in which:

either R$_1$ represents a C$_1$-C$_7$ alkyl group, a C$_2$-C$_7$ alkenyl group, or a C$_2$-C$_7$ alkenyl group carrying at least one substituent chosen from aryl groups, in which case R$_2$, which may be in the 3-, 6- or 8-position of the quinoline ring, represents a C$_3$-C$_7$ alkenyl group substituted with one or more C$_1$-C$_7$ alkoxy groups, or a C$_2$-C$_{10}$ alkynyl group substituted with a heteroaryl group;

or R$_1$ represents a C$_1$-C$_7$ alkyl group carrying at least one substituent chosen from hydroxyl, amine, C$_1$-C$_4$ alkoxy and C$_1$-C$_4$ aminoalkyl groups, or R$_1$ represents a C$_2$-C$_7$ alkenyl group carrying at least one substituent chosen from hydroxyl, amine, C$_1$-C$_4$ alkoxy and C$_1$-C$_4$ aminoalkyl groups, in which case R$_2$, which may be in the 3-, 6- or 8-position of the quinoline ring, represents a C$_3$-C$_7$ alkenyl group substituted with one or more $C_1$-$C_7$ alkoxy groups, or a $C_2$-$C_{10}$ alkynyl group, the latter being optionally substituted with a heteroaryl group;

or $R_1$ represents:

a methyl or ethyl group carrying at least one substituent chosen from halogens;

in which case $R_2$, which may be in the 3-, 6- or 8-position of the quinoline ring, represents a $C_1$-$C_7$ alkoxy group, amine group, $C_1$-$C_{10}$ alkylamide group or $C_2$-$C_7$ alkenyl group substituted with one or more $C_1$-$C_7$ alkoxy groups, or else a $C_2$-$C_{10}$ alkynyl group substituted with a heteroaryl group;

or $R_1$ represents:

a 2-pyridyl radical in which case $R_2$, which may be in the 3-, 6- or 8-position of the quinoline ring, represents a hydrogen or halogen atom, formyl, carboxyl, $C_1$-$C_7$ alkyl, $C_1$-$C_7$ alkoxy, amine, $C_1$-$C_{10}$ alkylamide or $C_2$-$C_7$ alkenyl optionally substituted with one or more $C_1$-$C_7$ alkoxy groups, or else a $C_2$-$C_{10}$ alkynyl group, the latter being optionally substituted with a heteroaryl group:

or $R_1$ represents:

a $C_8$-$C_{15}$ alkyl group optionally carrying a substituent chosen from aryl groups; or else a $C_8$-$C_{15}$ alkenyl group, a $C_2$-$C_7$ alkenyl group carrying at least one substituent chosen from arylsulfones; or else a $C_2$-$C_{15}$ alkynyl group, a $C_2$-$C_7$ alkynyl group carrying at least one substituent chosen from aryl and arylsulfone groups;

in which case $R_2$, which may be in the 3-, 6- or 8-position of the quinoline ring, represents a group chosen from a $C_1$-$C_7$ alkoxy, an amine, a $C_1$-$C_{10}$ alkylamide and a $C_2$-$C_7$ alkenyl optionally substituted with one or more $C_1$-$C_7$ alkoxy groups, or else a $C_2$-$C_{10}$ alkynyl group substituted with a heteroaryl group;

or $R_1$ represents:

a hydrogen atom, a formyl group or a heteroaryl group optionally substituted with one or more hydroxyl groups, with the exception of the 2-pyridyl radical; or else a $C_1$-$C_{15}$ alkyl group carrying at least one substituent chosen from oxygen and formyl, carboxyl, aryloxycarbonyl, $C_2$-$C_8$ alkyloxycarbonyl, $C_3$-$C_9$ alkenyloxycarbonyl, nitrile, phenoxy, $C_3$-$C_6$ cycloalkyl, heteroaryloxy, arylsulfone, $C_1$-$C_7$ alkylsulfone and $C_1$-$C_7$ thioalkyl groups, a $C_1$-$C_7$ alkyl group carrying at least one substituent chosen from $C_5$-$C_7$ alkoxy and $C_5$-$C_7$ aminoalkyl groups, a $C_3$-$C_{15}$ alkyl group carrying at least one substituent chosen from halogens, a $C_6$-$C_{15}$ alkyl group substituted with at least one heteroaryl group, a $C_8$-$C_{15}$ alkyl group carrying at least one substituent chosen from hydroxyl, amine, $C_1$-$C_7$ alkoxy and $C_1$-$C_7$ aminoalkyl groups; or else a $C_2$-$C_7$ alkenyl group carrying at least one substituent chosen from oxygen, halogens and formyl, carboxyl, aryloxycarbonyl, $C_2$-$C_8$ alkyloxycarbonyl, $C_3$-$C_9$ alkenyloxycarbonyl, nitrile, phenoxy, $C_3$-$C_6$ cycloalkyl, heteroaryloxy, $C_1$-$C_7$ alkylsulfone, $C_1$-$C_7$ thioalkyl, $C_1$-$C_7$ alkoxy and $C_5$-$C_7$ aminoalkyl groups; a $C_3$-$C_7$ alkenyl group substituted with a heteroaryl group; or else a $C_2$-$C_7$ alkynyl group carrying at least one substituent chosen from oxygen, halogens and hydroxyl, formyl, carboxyl, aryloxycarbonyl, $C_2$-$C_8$ alkyloxycarbonyl, $C_3$-$C_9$ alkenyloxycarbonyl, nitrile, heteroaryl, $C_1$-$C_7$ alkylsulfone, $C_1$-$C_7$ thioalkyl and $C_1$-$C_7$ aminoalkyl groups; or else a $C_2$-$C_{15}$ alkenyl or alkynyl group substituted with at least one $C_1$-$C_7$ trialkylsilyl group;

in which case $R_2$, which may be in the 3-, 6- or 8-position of the quinoline ring, represents a hydrogen or halogen atom, a hydroxyl group, a formyl group, a carboxyl group, a $C_1$-$C_7$ alkyl group, a $C_1$-$C_7$ alkoxy group, an amine group, a $C_1$-$C_{10}$ alkylamide group or a $C_2$-$C_7$ alkenyl group optionally substituted with one or more $C_1$-$C_7$ alkoxy groups, or else a $C_2$-$C_{10}$ alkynyl group, the latter being optionally substituted with a heteroaryl group; or one of its pharmaceutically acceptable salts, for use as medicinal products.

Here again, use is preferably made of a quinoline in which the carbon atom in the 2-position of the quinoline ring is substituted with an unsaturated hydrocarbon-based chain, and in particular a quinoline in which:

either $R_1$ represents:

a $C_2$-$C_7$ alkenyl group optionally substituted with one or more groups chosen from hydroxyl, amine, aryl, $C_1$-$C_4$ alkoxy and $C_1$-$C_4$ aminoalkyl groups, in which case $R_2$ represents a $C_3$-$C_7$ alkenyl group substituted with one or more $C_1$-$C_7$ alkoxy groups, or a $C_2$-$C_{10}$ alkynyl group, the latter being optionally substituted with a heteroaryl group;

or $R_1$ represents:

a $C_2$-$C_7$ alkenyl group carrying at least one substituent chosen from oxygen, halogens and formyl, carboxyl, $C_2$-$C_8$ alkyloxycarbonyl, nitrile, phenoxy, $C_3$-$C_6$ cycloalkyl, heteroaryloxy, $C_1$-$C_7$ alkylsulfone, $C_1$-$C_7$ thioalkyl, $C_5$-$C_7$ alkoxy and $C_5$-$C_7$ aminoalkyl groups;

a $C_3$-$C_7$ alkenyl group substituted with a heteroaryl group; or else a $C_2$-$C_7$ alkynyl group carrying at least one substituent chosen from oxygen, halogens and hydroxyl, formyl, carboxyl, $C_2$-$C_8$ alkyloxycarbonyl, nitrile, heteroaryl, $C_1$-$C_7$ alkylsulfone, $C_1$-$C_7$ thioalkyl and $C_1$-$C_7$ aminoalkyl groups; or else a $C_2$-$C_{15}$ alkenyl or alkynyl group substituted with at least one $C_1$-$C_7$ trialkylsilyl group;

in which case $R_2$ represents a hydrogen atom, a hydroxyl group or a $C_1$-$C_7$ alkyl group.

Particularly preferably, $R_1$ represents a $C_2$-$C_7$ alkenyl or alkynyl group substituted with one or more halogen atoms, in particular chlorine, bromine or fluorine atoms.

The invention encompasses, for use as medicinal products, both known quinolines and novel quinolines.

Consequently, a subject of the present invention is also a novel quinoline, which is characterized in that it corresponds to general formula (I) represented above, in which:

either $R_1$ represents a 2-formylethen-1-yl, 2-oxopropyl, 2-hydroxypropyl, cyclopropylhydroxymethyl, 4-chlorobut-3-en-1-yn-1-yl, hept-1-en-1-yl, 2-bromo-ethenyl, 2-bromoethynyl, 2-bromo-2-fluoroethenyl, 4-methyl carboxylate buta-1,3-dien-1-yl, dec-1-yn-1-yl, 2-(2-quinoleyl)ethenyl or 2-(trimethylsilylethynyl)-4-trimethylsilylbut-1-en-3-yn-1-yl group, in which case $R_2$ represents a hydrogen atom;

or $R_1$ represents a prop-1-en-1-yl group, in which case $R_2$ represents a methyl group in the 6-position or a hydroxyl group in the 8-position of the quinoline ring;

or $R_1$ represents a 2-hydroxypropyl group, in which case $R_2$ represents a hydroxyl group in the 8-position of the quinoline ring;

or else $R_1$ represents a 2-methyl carboxylate ethenyl group, in which case $R_2$ represents a methyl group in the 6-position of the quinoline ring.

A subject of the present invention is also a pharmaceutical composition comprising, as active principle, at least one novel quinoline as defined above.

Other advantages and characteristics of the invention will become apparent on reading the further description which follows and which refers to examples of preparation of substituted quinolines which fall within the context of the invention and of demonstration of their biological activity in vitro.

It goes without saying, however, that these examples are given only by way of illustrations of the invention and in no way constitute a limitation thereof.

I—PREPARATION OF SUBSTITUTED QUINOLINE

EXAMPLE 1

Preparation of 2-(2-quinolyl)trimethylsilylacetylene

[Quinoline of General Formula (I) in which $R_1$=C≡C—Si$(CH_3)_3$ and $R_2$=H]

0.6 g (4.13 mmol) of quinoline N-oxide is dissolved in 15 ml of anhydrous tetrahydrofuran (THF) at 20° C., in a dry round-bottomed flask equipped with a magnetic stirrer and a nitrogen inlet. The resulting solution is treated with 0.64 mol (4.96 mmol) of isobutyl chloroformate and the suspension obtained is cooled to −78° C.

6.23 ml of a solution of trimethylsilylethynyl magnesium bromide in THF (prepared from a mixture of 1.28 ml (9 mmol) of trimethylsilylacetylene and 4.95 ml (9.9 mmol) of a 2M solution of butyl magnesium bromide in THF) are then added dropwise. After stirring for 90 minutes at −78° C., the solution is slowly brought back to ambient temperature (30 minutes), and then hydrolyzed in 15 ml of water.

After separation of the two phases, the aqueous phase is extracted with diethyl ether (5×50 ml). The organic phases are pooled, the solvent is evaporated off and the residue is taken up with 10 ml of sulfuric acid (2M). The acid solution is extracted with dichloromethane (2×75 ml). The aqueous phase is then brought back to pH=9 with a saturated $K_2CO_3$ solution, and extracted with dichloromethane (2×50 ml).

The organic phases derived from the acid extraction are pooled, washed with a saturated $K_2CO_3$ solution and then a saturated NaCl solution, dried over magnesium sulfate ($MgSO_4$), filtered and concentrated.

The organic phases derived from the extraction with base are washed with a saturated NaCl solution, dried over magnesium sulfate ($MgSO_4$), filtered and concentrated.

The two reaction crudes are pooled and purified by medium pressure chromatography on silica gel using as eluent: cyclohexane/ethyl acetate: 95/5, so as to obtain 0.696 g of 2-(2-quinolyltrimethylsilylacetylene.

Yield: 75%. Empirical formula: $C_{14}H_{15}NSi$. $^1H$ NMR (200 MHz, $CDCl_3$)-δ ppm: 0.30 (s, 9H); 7.52 (m, 2H); 7.72 (m, 2H); 8.08 (d, J=8.4 Hz, 1H); 8.1 (d, J=8.3 Hz, 1H). $^{13}C$ NMR (50 MHz, $CDCl_3$)-δ ppm: −0.35; 95.50; 104.19; 124.23; 127.02; 127.50; 127.31; 129.26; 129.84; 135.90; 143.09; 147.94. IC-MS ($NH_4^+$): 225 ($M^+$, 100). IR ($cm^{-1}$): 2955; 2155; 1590; 1555; 1500; 1455; 1420; 1375; 1330; 1305; 1245; 1220; 1115; 955; 905; 840; 820; 790; 765; 745; 700; 635.

EXAMPLE 2

Preparation of 1-(2-quinolyl)acetylene

[Quinoline of General Formula (I) in which $R_1$=C≡CH and $R_2$=H]

0.075 g (0.33 mmol) of 2-(2-quinolyl)trimethylsilylacetylene, obtained as described in Example 1, is dissolved in 8 ml of anhydrous THF, in a dry round-bottomed flask equipped with a magnetic stirrer and a nitrogen inlet. Added to this solution is 0.36 mol (0.36 mmol) of n-tetrabutylammonium fluoride from a 1M solution in tetrahydrofuran. After stirring for 15 minutes at ambient temperature, the reaction is hydrolyzed with 10 ml of water.

After separation of the two phases, the aqueous phase is extracted with ethyl acetate (4×50 ml).

The organic phases are pooled, washed with a saturated sodium hydrogen carbonate ($NaHCO_3$) solution and then a saturated NaCl solution, dried over magnesium sulfate ($MgSO_4$), filtered and concentrated.

The reaction crude obtained is purified by medium pressure chromatography on silica gel using as eluent: cyclohexane/ethyl acetate: 80/20, so as to obtain 0.045 g of 1-(2-quinolyl)acetylene.

Yield: 88%. Empirical formula: $C_{11}H_7N$. $^1H$ NMR (400 MHz, $CDCl_3$)-δ ppm: 3.25 (s, 1H, H-2'); 7.55 (d, J=8.7 Hz, 1H, H-3); 7.56 (t, J=7.7 Hz, 1H, H-6); 7.74 (dd, J=7.6 Hz, 1H, H-7); 7.81 (d, J=8.1 Hz, 1H, H-5); 8.11 (d, J=8.8 Hz, 1H, H-8); 8.4 (d, J=8.7 Hz, 1H, H-4). $^{13}C$ NMR (50 MHz, $CDCl_3$)-δ ppm: 77.48 (C-2'); 83.11 (C-1'); 123.80 (C-3); 127.04 (C-6); 127.18 (C-5); 127.40 (C-10); 128.97 (C-8); 129.78 (C-7); 135.91 (C-4); 142.06 (C-2); 147.68 (C-9). ESI-MS ($NH_4^+$): 154 ($MH^+$, 100). IR ($cm^{-1}$): 3165; 2105; 1615; 1595; 1555; 1500; 1420; 1375; 1330; 1305; 1255; 1210; 1140; 1115; 955; 830; 620.

EXAMPLE 3

Preparation of Methyl E-3-(2-quinolyl)-2-propenoate

[Quinoline of General Formula (I) in which $R_1$=—CH=CH—$C(O)OCH_3$ and $R_2$=H]

0.2 g (1.27 mmol) of 2-formylquinoline is dissolved in 10 ml of anhydrous toluene, in a dry round-bottomed flask equipped with a magnetic stirrer and a nitrogen inlet. 0.51 g (1.52 mmol) of methyl(triphenylphosphoranylidene) acetate is added. The reaction mixture is brought to the reflux temperature of toluene for 90 minutes, and the solution is then slowly returned to ambient temperature and hydrolyzed with 10 ml of water.

After separation of the two phases, the aqueous phase is extracted with ethyl acetate (4×50 ml). The pooled organic phases are washed with a saturated sodium hydrogen carbonate ($NaHCO_3$) solution and then a saturated NaCl solution, dried over magnesium sulfate ($MgSO_4$), filtered and concentrated.

The reaction crude obtained is purified by medium pressure chromatography on silica gel using as eluent: cyclohexane/ethyl acetate: 70/30, so as to obtain 0.216 g of methyl E-3-(2-quinolyl)-2-propenoate.

Yield: 80%. Empirical formula: $C_{14}H_{11}NO_2$. $^1H$ NMR (200 MHz, $CDCl_3$)-δ ppm: 3.85 (s, 3H, OMe); 7.00 (d, J=14.9 Hz, 1H, H-2'); 7.54 (t, J=7.9 Hz, 1H, H-6); 7.57 (d, J=8.7 Hz, 1H, H-3); 7.72 (dd, J=7.2, 8.1 Hz, 1H, H-7); 7.78 (d, J=8.1 Hz, 1H, H-5); 7.89 (d, J=16.0 Hz, 1H, H-1'); 8.10

(d, J=8.5 Hz, H-8); 8.14 (d, J=8.5 Hz, H-4). $^{13}$C NMR (50 MHz, CDCl$_3$)-δ ppm: 51.67 (OMe); 120.12 (C-3); 123.01 (C-2'); 127.11 (C-6); 127.33 (C-5); 127.87 (C-10); 129.67 (C-8); 129.83 (C-7); 136.48 (C-4); 144.11 (C-1'); 148.06 (C-9); 152.88 (C-2); 166.74 (C-3'). ESI-MS: 214 (MH$^+$, 100). IR (cm$^{-1}$): 1740 (C=O); 1725; 1650; 1595; 1560; 1500; 1435; 1345; 1245; 1195; 1155; 975; 825; 755; 715; 620.

EXAMPLE 4

Preparation of E-3-(2-quinolyl)prop-2-en-1-ol

[Quinoline of General Formula (I) in which R$_1$=—CH=CH—CH$_2$OH and R$_2$=H]

0.2 g (0.93 mmol) of methyl E-3-(2-quinolyl)-2-propenoate obtained as described in Example 3 is dissolved in 10 ml of anhydrous toluene, in a dry round-bottomed flask equipped with a magnetic stirrer and a nitrogen inlet. The solution is cooled to −78° C. and then 1.87 ml (1.87 mmol) of diisobutylaluminum hydride in a 1M solution in toluene are added dropwise. After stirring for 2 hours, 5 ml of methanol are added, the solution is then brought back to ambient temperature and 50 ml of ethyl acetate are added, the hydrolysis is continued overnight and the solution is then filtered over celite. The filtrate is extracted with ethyl acetate (2×25 ml).

The organic phases are pooled, washed with a saturated sodium hydrogen carbonate (NaHCO$_3$) solution and then a saturated NaCl solution, dried over magnesium sulfate (MgSO$_4$), filtered and concentrated.

The reaction crude obtained is purified by medium pressure chromatography on silica gel using as eluent: cyclohexane/ethyl acetate: 60/40, so as to obtain 0.085 g of E-3-(2-quinolyl)prop-2-en-1-ol.

Yield: 49%. Empirical formula: C$_{12}$H$_{11}$NO. $^1$H NMR (200 MHz, CDCl$_3$)-δ ppm: 4.44 (d, J=3.9 Hz, 2H, H-3'); 6.87 (dt, J=16.8, 4.3 Hz, 1H, H-2'); 7.01 (d, J=16.3 Hz, 1H, H-1'); 7.44 (unresolved peak, 2H); 7.67 (unresolved peak, 2H); 7.57 (unresolved peak, 2H). $^{13}$C NMR (50 MHz, CDCl$_3$)-δ ppm: 62.60 (C-3'); 118.90; 126.15; 127.21; 127.40; 128.73; 129.73; 130.11; 136.48; 137.21; 147.67; 155.71.

ESI-MS: 208 (M+Na, 12); 186 (MH$^+$, 100).

IR (cm$^{-1}$): 3145; 2835; 1650; 1615; 1600; 1560; 1505; 1430; 1370; 1315; 1150; 1120; 1095; 965; 930; 840; 810; 770; 745; 635; 605.

EXAMPLE 5

Preparation of 3-(2-quinolyl)propenal

[Quinoline of General Formula (I) in which R$_1$=—CH=CH—COH and R$_2$=H]

0.2 g (1.27 mmol) of 2-formylquinoline is dissolved in 10 ml of anhydrous toluene, in a dry round-bottomed flask equipped with a magnetic stirrer and a nitrogen inlet. 0.46 g (1.52 mmol) of (triphenylphosphoranylidene)acetaldehyde is added to this solution. The mixture is brought back to the reflux temperature of toluene for 90 minutes, and the solution is then slowly brought back to ambient temperature and hydrolyzed with 10 ml of water. After separation of the two phases, the aqueous phase is extracted with ethyl acetate (4×50 ml).

The organic phases are pooled, washed with a saturated sodium hydrogen carbonate (NaHCO$_3$) solution and then a saturated NaCl solution, dried over magnesium sulfate (MgSO$_4$), filtered and concentrated.

The reaction crude obtained is purified by medium pressure chromatography on silica gel using as eluent: cyclohexane/ethyl acetate: 75/25, so as to obtain 0.137 g of 3-(2-quinolyl)propenal.

Yield: 60%. Empirical formula: C$_{12}$H$_9$NO. $^1$H NMR (400 MHz, CDCl$_3$)-δ ppm: 7.13 (ddd, J=16.2, 7.7, 0.7 Hz, 1H, H-2'); 7.59 (dd, J=7.0, 7.0 Hz, 1H, H-6); 7.69 (d, J=8.5 Hz, 1H, H-3); 7.73 (d, J=16.1 Hz, 1H, H-1'); 7.76 (dd, J=7.2, 7.5 Hz, 1H, H-7); 7.84 (d, J=8.1 Hz, 1H, H-5), 8.12 (d, J=8.5 Hz, 1H, H-8); 8.22 (d, J=8.5 Hz, 1H, H-4); 9.86 (dd, J=7.7, 0.7 Hz, 1H, H-3'). $^{13}$C NMR (50 MHz, CDCl$_3$)-δ ppm: 119.85 (C-3); 127.52 (C-5); 127.78 (C-6); 128.11 (C-10); 129.91 (C-8); 130.22 (C-7); 132.54 (C-2'); 136.84 (C-4); 148.28 (C-9); 151.75 (C-1'); 152.84 (C-2); 193.52 (C-3'). ESI-MS: 184 (MH$^+$, 100). IR (cm$^{-1}$): 3050; 1670 (C=O); 1630; 1595; 1555; 1500; 1430; 1290; 1125; 1110; 980; 900; 825; 785; 625; 590.

EXAMPLE 6

Preparation of (2-quinolyl)ethylene

[Quinoline of General Formula (I) in which R$_1$=—CH=CH$_2$ and R$_2$=H]

0.8 g (5.51 mmol) of quinoline N-oxide is dissolved in 15 ml of anhydrous THF at 20° C., in a dry round-bottomed flask equipped with a magnetic stirrer and a nitrogen inlet. This solution is treated with 0.78 ml (6.07 mmol) of isobutyl chloroformate; the suspension obtained is cooled to −78° C. 11 ml (11 mmol) of a 1M solution of vinylmagnesium bromide in THF are then added dropwise. After stirring for 90 minutes at −78° C., the solution is slowly returned to ambient temperature (30 minutes), and then hydrolyzed with 15 ml of water.

After separation of the two phases, the aqueous phase is extracted with diethyl ether (5×50 ml). The organic phases are pooled, the solvent is evaporated off and the residue is taken up with 10 ml of sulfuric acid (2M). The acid solution is extracted with dichloromethane (2×75 ml) and the aqueous phase is brought back to pH=9 with a saturated K$_2$CO$_3$ solution, and then extracted with CH$_2$Cl$_2$ (2×50 ml).

The organic phases derived from the acid extraction are pooled, washed with a saturated K$_2$CO$_3$ solution and then a saturated NaCl solution, dried over magnesium sulfate (MgSO$_4$), filtered and concentrated.

The organic phases derived from the extraction with base are washed with a saturated NaCl solution, dried over magnesium sulfate (MgSO$_4$), filtered and concentrated.

The two reaction crudes are pooled and purified by medium pressure chromatography on silica gel using as eluent: cyclohexane/ethyl acetate: 95/5, so as to obtain 0.126 g of (2-quinolyl)ethylene.

Yield: 82%. Empirical formula: C$_{11}$H$_9$N. $^1$H NMR (200 MHz, CDCl$_3$)-δ ppm: 5.66 (d, J=10.9 Hz, 1H, H-2'a); 6.27 (d, J=17.7 Hz, 1H, H-2'b); 7.04 (dd, J=17.7, 11.1 Hz, 1H, H-1'); 7.49 (t, J=7.2 Hz, 1H, H-6); 7.60 (d, J=8.7 Hz, 1H, H-3); 7.69 (dd, J=7.2, 8.1 Hz, 1H, H-7); 7.77 (d, J=7.9 Hz, 1H, H-5); 8.06 (d, J=9.8 Hz, 1H, H-8); 8.11 (d, J=8.0 Hz, 1H, H-4). $^{13}$C NMR (50 MHz, CDCl$_3$)-δ ppm: 118.24 (C-3); 119.66 (C-2'); 126.17 (C-6); 127.11 (C-10); 127.32 (C-5); 129.22 (C-8); 129.46 (C-7); 136.17 (C-4); 137.87 (C-1'); 147.93 (C-9); 155.96 (C-2). IR (cm$^{-1}$): 1615; 1595; 1555; 1505; 1425; 1310; 1140; 1120; 1015; 990; 925; 830; 760; 715; 730; 615.

EXAMPLE 7

Preparation of E-1-(2-quinolyl)butene

[Quinoline of General Formula (I) in which $R_1$=—CH=CH—CH$_2$—CH$_3$ and $R_2$=H]

4.90 g (12.7 mmol) of propyltriphenylphosphonium bromide are suspended in 15 ml of anhydrous toluene at 0° C., in a dry round-bottomed flask equipped with a magnetic stirrer and a nitrogen inlet, and then 1.71 g (15.2 mmol) of potassium tert-butoxide (tBuOK) are added. After stirring for 15 minutes, a solution at 0° C. containing 1 g (6.36 mol) of 2-formylquinoline in 10 ml of anhydrous tetrahydrofuran is added. The reaction mixture is brought to the reflux temperature of toluene for 90 minutes, and the solution is then slowly brought back to ambient temperature and hydrolyzed with 20 ml of water.

After separation of the two phases, the aqueous phase is extracted with ethyl acetate (4×50 ml).

The organic phases are pooled, washed with a saturated sodium hydrogen carbonate (NaHCO$_3$) solution and then a saturated NaCl solution, dried over magnesium sulfate (MgSO$_4$), filtered and concentrated.

The reaction crude obtained is purified by medium pressure chromatography on silica gel using as eluent: cyclohexane/ethyl acetate: 92/8, so as to obtain 0.674 g of E-1-(2-quinolyl)butene.

Yield: 58%. Empirical formula: C$_{13}$H$_{13}$N. $^1$H NMR (400 MHz, CDCl$_3$)-δ ppm: 1.17 (t, J=7.5 Hz, 3H, H-4'); 2.36 (dqd, J=7.5, 6.3, 1.5 Hz, 1H, H-3'); 6.72 (dt, J=15.9, 1.5 Hz, 1H, H-1'); 6.88 (dd, J=15.9, 6.3 Hz, 1H, H-2'); 7.45 (ddd, J=6.9, 6.9, 1.2 Hz, 1H, H-6); 7.52 (d, J=8.6 Hz, 1H, H-3); 7.66 (ddd, J=6.9, 6.9, 1.5 Hz, 1H, H-7); 7.74 (dd, J=8.01, 1.3 Hz, 1H, H-5); 8.03 (dd, J=9.4 Hz, 1H, H-8); 8.06 (d, J=9.0 Hz, 1H, H-4). $^{13}$C NMR (50 MHz, CDCl$_3$)-δ ppm: 12.90 (C-4'); 25.80 (C-3'); 118.46 (C-3); 125.54 (C-6); 126.90 (C-10); 127.18 (C-5); 128.88 (C-8); 129.21 (C-7); 129.92 (C-1'); 135.84 (C-4); 139.00 (C-2'); 147.87 (C-9); 156.30 (C-2). ESI-MS: 184 (MH$^+$, 100). IR (cm$^{-1}$): 2965; 1650; 1615; 1595; 1555; 1505; 1460; 1425; 1315; 1115; 965; 855; 815; 750; 620.

EXAMPLE 8

Preparation of E-1-bromo-2-(2-quinolyl)-ethene

[Quinoline of General Formula (I) in which $R_1$=—CH=CH—Br and $R_2$=H]

0.2 g (6.38×10$^{-4}$ mol) of 1,1-dibromo-2-(2-quinolyl) ethene obtained from 2-formylquinoline, carbon tetrabromide (CBr$_4$) and triphenylphosphine (PPh$_3$) (Ramirez et al., J. Am. Chem. Soc., 1962, 84: 1745) and 11.28 mg (3.19× 10$^{-5}$ mol, 5 mol %) of iron triacetylacetonate (Fe(acac)$_3$) are dissolved in 3 ml of anhydrous THF and 3 ml of anhydrous N-methylpyrrolidone (NMP) at −10° C., in a dry round-bottomed flask equipped with a magnetic stirrer and a nitrogen inlet. 0.39 ml (7.02×10$^{-4}$ mol) of a 1.8M solution of isopropyl magnesium bromide in THF is added dropwise to the solution. After stirring for 30 minutes, the reaction is hydrolyzed with 10 ml of water and the solution is brought back to ambient temperature. Next, the two phases are separated and the aqueous phase is extracted with diethyl ether (3×30 ml).

The organic phases are pooled, washed with a saturated sodium hydrogen carbonate (NaHCO$_3$) solution and then a saturated NaCl solution, dried over magnesium sulfate (MgSO$_4$), filtered and concentrated.

The reaction crude obtained is purified by medium pressure chromatography on silica gel using as eluent: hexane/ethyl acetate: 92/8, so as to obtain 0.125 g of E-1-bromo-2-(2-quinolyl)ethene.

Yield: 84%. Empirical formula: C$_{11}$H$_8$NBr. $^1$H NMR (400 MHz, CDCl$_3$)-δ ppm: 7.36 (d, J=8.37 Hz, 1H); 7.37 (d, J=15.9 Hz, 1H); 7.50 (d, J=13.7 Hz, 1H); 7.52 (t, J=3.55 Hz, 1H); 7.70 (t, J=7.5 Hz, 1H); 7.76 (d, J=8.11 Hz, 1H); 8.04 (d, J=8.5 Hz, 1H); 8.10 (d, J=8.4 Hz, 1H). $^3$C NMR (50 MHz, CDCl$_3$)-δ ppm: 114.14 (C-2'); 119.24 (C-3); 126.51 (C-6); 126.75 (C-5); 127.51 (C-10); 129.35 (C-8); 129.97 (C-7); 136.71 (C-4); 137.53 (C-1'); 147.06 (C-9); 154.00 (C-2). ESI-MS: 236 (MH$^+$, 100); 234 (MH$^+$, 78). IR (cm$^{-1}$): 3055; 1605; 1590; 1550; 1500; 1425; 1305; 1440; 1115; 935; 835; 800; 775; 745; 620; 575.

II—Biological Activity In Vitro of the Substituted Quinolines

The antiprotozoan biological activity of the substituted quinolines was demonstrated on:

- amastigotes of *Leishmania amazonensis* (WHO reference: MPRO/BR/1972/M1841), of *Leishmania donovani* (MHOM/ET/67/L82) and of *Leishmania infantum* (MHOM/MA(BE)67 and IPZ229/1/89);
- amastigotes of *Trypanosoma cruzi* (Tulahuen strain) and circulating forms of *Trypanosoma brucei* (S427 strain).

Their antiretroviral activity was, itself, demonstrated on CEM4fx cells infected with the molecular clone pLN4-3 of the human immunodeficiency virus (HIV-1).

1) Substituted Quinolines Tested:

The substituted quinolines whose biological activity was tested are represented in Table I below.

TABLE I

| Number | Molecular weight | $R_1$ | $R_2$ |
|---|---|---|---|
| 1 | 153 | 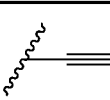 | H |
| 2 | 155 | 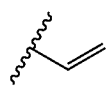 | H |

TABLE I-continued
| Number | Molecular weight | R₁ | R₂ |
|---|---|---|---|
| 4 | 169 | H | 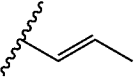 |
| 5 | 171 | 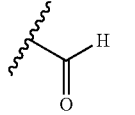 | CH₃ in the 6-position |
| 6 | 183 | 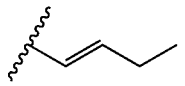 | H |
| 7 | 183 | 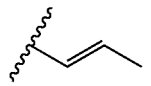 | CH₃ in the 6-position |
| 8 | 183 | 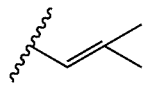 | H |
| 9 | 183 | 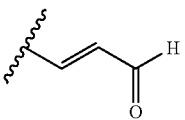 | H |
| 10 | 185 | 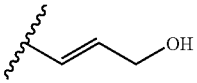 | H |
| 11 | 185 | 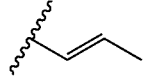 | OH in the 8-position |
| 13 | 185 | 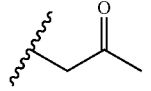 | H |
| 14 | 185 | H | 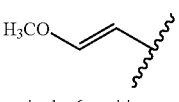<br>in the 6-position |
| 15 | 187 | 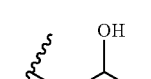 | H |
| 16 | 187 | 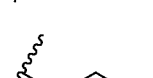 | H |
| 17 | 187 | 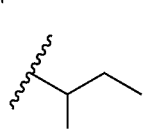 | H |
| 18 | 197 | 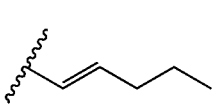 | H |

TABLE I-continued
| Number | Molecular weight | R₁ | R₂ |
|---|---|---|---|
| 19 | 199 | 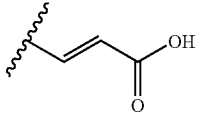 | H |
| 20 | 199 | 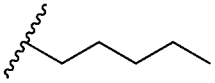 | H |
| 21 | 201 | 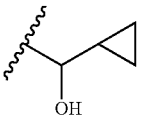 | H |
| 22 | 203 | 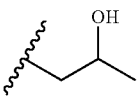 | OH in the 8-position |
| 23 | 213 | 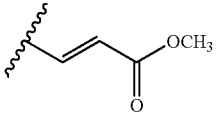 | H |
| 24 | 213 | 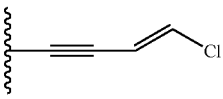 | H |
| 25 | 225 | 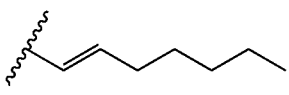 | H |
| 26 | 225 | 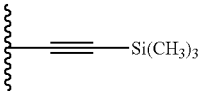 | H |
| 27 | 227 | 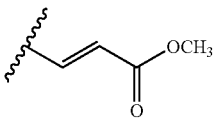 | $CH_3$ in the 6-position |
| 28 | 231.9 | 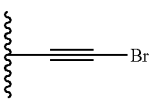 | H |
| 29 | 233.9 | 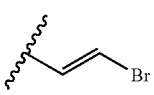 | H |
| 30 | 239 | 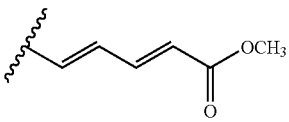 | H |
| 31 | 251.9 | 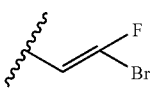 | H |

TABLE I-continued

| Number | Molecular weight | R₁ | R₂ |
|---|---|---|---|
| 32 | 265 | 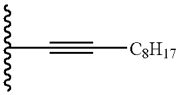 | H |
| 33 | 265 | H | 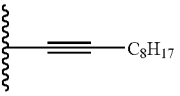<br>in the 3-position |
| 34 | 277 | 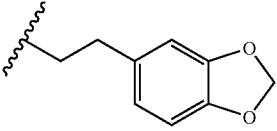 | H |
| 35 | 282 | 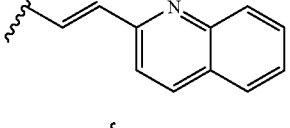 | H |
| 36 | 313 | 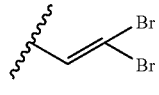 | H |
| 37 | 332 | H | 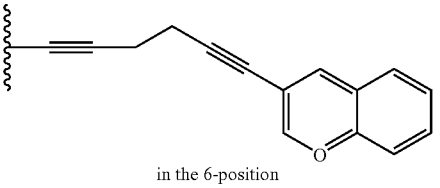<br>in the 6-position |
| 38 | 345 | 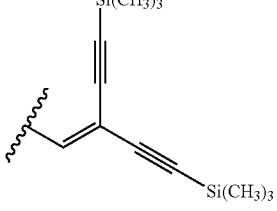 | H |

2) Experimental Protocols:

a) Tests Carried Out on Amastigotes of *Leishmania amazonensis*:

The strain of *Leishmania amazonensis* is maintained by successive passages in "nude" mice (nu/nu). The amastigotes are isolated from the lesions developed on the footpads, and purified according to the method described by Antoine et al. (*Parasitology*, 1989, 99: 1).

The macrophages, which will be used as host cells for the leishmania, are obtained after multiplication and differentiation of medullary precursors from BALB/c mice. This culture is prepared in the presence of supernatant from a conditioned line of fibroblasts L-929, and source of "Macrophage Colony Stimulating Factor". After culturing for 5 days on a hydrophobic support, the adherent macrophages are recovered and then distributed in flat-bottomed 96-well plates for cell culture, in a proportion of $4 \times 10^4$ macrophages per well. The macrophages are then infected with purified amastigotes (4 parasites per macrophage) and incubated at 34° C. for 24 hours to allow development of parasitophorous vacuoles and multiplication of parasites. Under these conditions, more than 95% of the macrophages are infected.

The solutions of the substituted quinolines to be tested are prepared in DMSO before being added, at various concentrations, to the infected macrophage cultures. Serial 2-fold dilutions, from 100 µg/ml to #6 ng/ml, were used, and the final concentration of DMSO, which in all cases is 0.1%, was found to be nontoxic with respect to the macrophages.

The leishmanicidal activity of the quinolines is determined 30 hours after addition of the solutions of substituted quinolines. It is based on a more or less large, or even complete, decrease, firstly, in the size of the parasitophorous vacuoles and, secondly, in the number of live intracellular amastigotes. For each substituted quinoline tested, the 100% inhibitory concentration ($IC_{100}$) with respect to the parasites is thus determined.

b) Tests on Amastigotes of *Leishmania donovani* and *Leishmania infantum*

The *Leishmania donovani* and *Leishmania infantum* strains are maintained by successive passages in golden hamsters. The amastigotes are isolated from the spleens of the infected hamsters and brought into contact with the purified macrophages.

Twenty-four hours after intraperitoneal injection of Balb/c mice with a 2% starch solution, the peritoneal macrophages of these mice are collected, washed in Dulbecco PBS and then distributed in Lab-tek® culture chambers, in a proportion of $4\times10^4$ cells per 100 µl per well in RPMI-1640 medium supplemented with 10% of FCS and antibiotics. After 24 hours at 37° C. in a humid atmosphere (5% $CO_2$), the macrophages are brought into contact with purified amastigotes (3 parasites per macrophage) in a final volume of 200 µl for 4 hours. The medium is then removed in order to eliminate the extracellular parasites, and replaced with 100 µl of fresh medium.

Twenty-four hours after the beginning of infection, the solutions of substituted quinolines prepared as described in paragraph a) above are added and the leishmanicidal activity is determined after 48 hours by counting the number of parasites still alive in the fixed and Giemsa-stained cells. For each substituted quinoline tested, the 50% inhibitory concentration ($IC_{50}$) with respect to the parasites is thus determined.

c) Tests on Amastigotes of *Trypanosoma cruzi*

Peritoneal macrophages from Balb/c mice are collected, washed in Dulbecco PBS and then distributed in 96-well plates in a proportion of $3\times10^4$ cells per 100 µl and per well, in RPMI-1640 medium supplemented with 10% FCS and antibiotics.

After 24 hours at 37° C., $10^5$ trypomastigotes are added with serial 2-fold dilutions of the various substituted quinolines. The cultures are then incubated at 37° C. for 4 days in a humid atmosphere (5% $CO_2$-95% air). After fixing, and then staining with Giemsa, the antiparasitic activity is assessed by counting the extracellular trypomastigotes and the intracellular amastigotes. For each substituted quinoline tested, the 50% inhibitory concentration ($IC_{50}$) with respect to the parasites is thus determined.

d) Tests on the Circulating Forms of *Trypanosoma brucei*

The circulating forms of *Trypanosoma brucei* are cultured in MEM medium (minimum essential medium; GIBCO-BRL, No. 072-1100) to which Earle's salts have been added and supplemented with 1 mg/ml of glucose, 2.2 mg/ml of $NaHCO_3$, 10 mM of Hepes, 2 mM of sodium pyruvate, 0.2 mM of 2-mercaptoethanol, 0.1 mM of hypoxanthine and 15% of inactivated horse serum.

The cultures are maintained at 37° C. in 24-well plates in a humid atmosphere (5% $CO_2$-95% air) and the passages are carried out every 2 or 3 days at a density of $10^3$ to $10^5$ trypomastigotes per ml. The activity of the substituted quinolines is tested in triplicate in 96-well plates in which $10^3$ parasites originating from an exponential growth phase are distributed per well, in the presence of the various solutions of substituted quinolines in a final volume of 200 µl. After culturing for 48 hours, the trypanocidal activity is assessed by counting, with a Neubauer cell, the number of live parasites per well. For each substituted quinoline tested, the 50% inhibitory concentration ($IC_{50}$) with respect to the parasites is thus determined.

e) Tests on the Replication of HIV-1

CEM4fx cells are infected de novo with the molecular clone pLN4-3 of HIV-1, and simultaneously treated with the substituted quinolines to be tested, dissolved beforehand in DMSO. The virus multiplies for three days, and then the presence of infectious virions is detected in the culture supernatant (RPMI medium) by reinfecting "P4" cells which have a reporter gene which is expressed when they are infected with the virus. The viral load is quantified after culturing for 72 hours, by two methods: estimation of the viral load by infection of HeLa-βgal $CD_4^+$ cells and determination of the amount of viral protein p24 by an ELISA assay.

Moreover, the cytotoxicity of the quinolines with respect to the host cells is measured by an MTT [3-(4,5-dimethylthiazol-2-yl)-2,5-diphenyltetrazolium bromide]bioconversion assay. All the assays are carried out in triplicate.

3) Results:

The results obtained with the substituted quinolines, assigned Nos. 1, 2, 4, 6 to 11, 13 to 20, 23 to 34, 37 and 38 in Table I, are given in Table II below as regards their activity on the amastigotes of *Leishmania amazonensis*, of *Leishmania donovani* and of *Leishmania infantum*, and also their cytotoxicity with respect to the macrophages.

TABLE II

| Quinolines | *L. amazonensis* $IC_{100}$ (µg/ml) | Cytotoxicity on macrophages (µg/ml) | *L. donovani* $IC_{50}$ (µg/ml) | *L. infantum* (IPZ229/1/89) $IC_{50}$ (µg/ml) | *L. infantum* (MHOM/MA (BE) 67) $IC_{50}$ (µM) |
|---|---|---|---|---|---|
| 1 | 0.78125 | 6.25 | | | >32 |
| 2 | 3.12 | 6.25 | 1.2-2.8 | 1.3 | >32 |
| 4 | 25 | 25 | | | |
| 5 | | | | | 32 |
| 6 | 6.25 | 25 | | | |
| 7 | 12.5 | 25 | | | |
| 8 | 12.5 | 12.5 | | | |
| 9 | 0.781 | 1.56 | | | |
| 10 | 1.56 | 6.25 | | | 3 |
| 11 | 50 | 50 | | | 14 |
| 13 | 25 | 25 | | | |
| 14 | 25 | 100 | | | |
| 16 | 10-20 | | | | |
| 17 | | | | | 16 |
| 18 | 12.5 | 50 | | | >32 |

TABLE II-continued

| Quinolines | L. amazonensis IC$_{100}$ (µg/ml) | Cytotoxicity on macrophages (µg/ml) | L. donovani IC$_{50}$ (µg/ml) | L. infantum (IPZ229/1/89) IC$_{50}$ (µg/ml) | L. infantum (MHOM/MA (BE) 67) IC$_{50}$ (µM) |
|---|---|---|---|---|---|
| 19 | 12.5 | 12.5 | | | |
| 20 | >50 | >100 | | | 16 |
| 23 | 12.5 | 50 | 3.3-30 | 0.4-2.2 | 26 |
| 24 | 10-25 | | | | |
| 25 | 12.5 | 25 | | | 16 |
| 26 | 12.5 | 1.56 | 1.7 | 10.9 | 10 |
| 27 | 50 | | | | 10 |
| 28 | 12.5 | 12.5 | | | >32 |
| 29 | 0.78125 | 3.12 | | | 2 |
| 30 | 12.5 | 25 | | | >32 |
| 31 | 25 | 25 | | | |
| 32 | 12.5 | 12.5 | | | |
| 33 | 10-25 | | | | |
| 34 | 50 | 25 | | | 2 |
| 35 | | | | | 10 |
| 37 | 50-25 | | | 0.3-5.8 | 17 |
| 38 | 25 | 25 | | | |

A compound is considered to exhibit an advantageous activity on the amastigotes of Leishmania amazonensis when it exhibits an IC$_{100}$ of less than or equal to 25 µg/ml. It is, moreover, considered to exhibit an advantageous activity on the amastigotes of Leishmania donovani and infantum when it exhibits an IC$_{50}$ of less than or equal to 12.5 µg/ml.

The results obtained with the substituted quinolines, assigned Nos. 2, 6, 9 to 11, 13, 15, 17, 18, 20 to 23, 25, 28, 29 and 34 to 37 in Table I, are given in Table III below as regards their activity on the amastigotes of Trypanosoma cruzi and the circulating forms of Trypanosoma brucei.

TABLE III

| Quinolines | T. cruzi (amastigotes) IC$_{50}$ (µM) | T. brucei IC$_{50}$ (µM) |
|---|---|---|
| 1 | 8 | |
| 2 | 12 | 13 |
| 5 | >32 | |
| 6 | >32 | 17 |
| 9 | 5 | 19 |
| 10 | 4 | >32 |
| 11 | 19 | >32 |
| 13 | >32 | 10 |
| 15 | >32 | 16 |
| 17 | >32 | 3 |
| 18 | >32 | 16 |
| 20 | 19 | 13 |
| 21 | >32 | 14 |
| 22 | 16 | 16 |
| 23 | 15 | 16 |
| 25 | 11 | 4 |
| 26 | 8 | |
| 27 | 25 | |
| 28 | >32 | 5 |
| 29 | <0.5 | 1 |
| 30 | 26 | |
| 34 | 15 | 13 |
| 35 | >32 | 24 |
| 36 | 21 | 4 |
| 37 | >32 | 13 |

A compound is considered to exhibit an advantageous activity on the amastigotes of Trypanosoma cruzi when it exhibits an IC$_{50}$ of less than or equal to 20 µM. It is, moreover, considered to exhibit an advantageous activity on the circulating forms of Trypanosoma brucei when it exhibits an IC$_{50}$ of less than or equal to 5 µM.

The results obtained with the substituted quinolines assigned Nos. 9, 20 and 26 in Table I are given in Table IV below as regards their cytotoxicity with respect to the CEM4fx cells on their activity on the replication of HIV-1 in these cells.

TABLE IV

| Quinolines | Cytotoxicity IC$_{50}$ (µM) | Antiretroviral activity IC$_{50}$ (µM) |
|---|---|---|
| 9 | 2 | 0.6 |
| 20 | 9 | 2 |
| 26 | 3 | 0.9 |

As shown in Tables II and III, the antiprotozoan activity of the substituted quinolines varies, in most cases, as a function of the specificity of the parasites, or even of the strains, on which they are tested. Thus, for example, the quinoline assigned No. 23 exhibits marked activity of Leishmania amazonensis and Leishmania donovani and on the IPZ229/1/89 strain of Leishmania infantum, whereas its activity proves to be less advantageous on the MHOM/MA (BE)$_{67}$ strain of Leishmania infantum and on Trypanosoma cruzi and Trypanosoma brucei. Similarly, the substituted quinoline assigned No. 25 shows advantageous activity on Leishmania amazonensis, Trypanosoma cruzi and Trypanosoma brucei, whereas it appears to be less active on Leishmania infantum.

Thus, those skilled in the art will choose, as a function of the parasites responsible for the co-infection that they wish to treat, the substituted quinoline which appears to them to be the most suitable. They may also combine two or more different substituted quinolines in order to optimize the therapeutic response or to broaden the spectrum of therapeutic action.

II—Biological Activity of the Substituted Quinolines In Vivo a) Tests Carried Out on Laboratory Animals Infected with Cutaneous Leishmaniasis (Leishmania amazonensis):

1/Laboratory Animals

The experimental animals are male or female approximately 6- to 8-week-old Balb/c mice weighing 18-24 g, subsequently reared for reproduction in the animal house of the Instituto de Investigaciones en Ciencias de la Salud (IICS), Asuncion, Paraguay. Golden hamsters (*Mesocricetus auratus*) are used to maintain these strains and as reservoirs for *L. amazonensis* parasites.

2/Parasites

The Balb/c mice are infected with *Leishmania amazonensis* parasites, at the amastigote stage of the reference strain IFLA/BR/67/PH8, subcutaneously in the ventral pad of the right rear foot, the left foot remaining as a control. The amount of amastigotes inoculated is $2 \times 10^6$ amastigotes in 50 µl of phosphate buffer saline (PBS) for *L. amazonensis*.

3/Treatment of Cutaneous Leishmaniasis

The treatments begin once the infection is well established, mainly in general 5 to 6 weeks after inoculation of the *L. amazonensis* amastigotes. The reference medicinal product chosen is Glucantime® or meglumine antimoniate from Aventis (France).

The treatments are carried out in the following way (8 mice per group):

Glucantime® is administered subcutaneously at a concentration of 100 mg/kg or 28 mg of $Sb^v$/kg at a rate of one daily injection for 15 days;

the quinolines are administered orally at 25 mg/kg/day for 15 days, in two doses, in the morning and at midday.

The quinolines or the N-methylglucamine antimoniate (Glucantime®) are dissolved in a drop of Tween 80 to which phosphate buffer saline is added so as to obtain the desired concentration, and then 50 µl of the solution obtained are administered. The untreated control mice are given 50 µl of a solution of Tween 80 with PBS.

4/Parameters Studied

Measurement of the lesion: the diameters of the lesions on the infected foot and on the control foot are measured using a micrometer with 1/10 mm graduations, once a week for the duration of the experiment. The first measurements begin 48 hours after inoculation of the parasites. Calculating the difference in the two measurements gives the thickness of the lesion.

Counting the amastigote forms in the lesion: after the treatments have been stopped, the animals are sacrificed and the lesions are collected in a Petri dish, weighed, cut up into pieces and ground using a 10 ml Potter grinder in 5 ml of RPMI culture medium (Rosewall Park Medecine Institute, USA, Gibco). The 5 ml of puree obtained are centrifuged twice. The layer containing the amastigotes is subjected to counting of the number of parasites using a Neubauer cell. Five counts are performed on each amastigote layer. The number of amastigote forms is determined using the Stauber formula which takes into account the weight of the lesion:

A/N×W×coefficient of the Neubauer cell

A=number of amastigotes, N=number of nuclei W=weight of the lesion

The results are expressed by the calculation of the arithmetic mean of the diameters of the lesions measured once a week and, at the end of the protocol, after sacrifice of the mice, of the weights of the lesions and of the number of amastigotes. A Student's test (t-test) is used for the statistical analysis of all the data. The comparison is made between "control" groups with a "treatment" group per pair. A value of P<0.05 is considered to be statistically significant.

FIG. 1 illustrates the effects of the treatments with Glucantime (28 mg of $Sb^v$/kg/day) administered subcutaneously, and E-1-(2-quinolyl)butene (6) and methyl E-3-(2-quinolyl)-2-propenate (23) administered orally at 25 mg/kg/day, for 15 days on Balb/c mice infected (n=8) with *L. amasonensis*.

Table V summarizes the effect of the treatments with Glucantime, E-1-(2-quinolyl)butene (6) and methyl E-3-(2-quinolyl)-2-propenate (23) on Balb/c mice infected (n=8) with *L. amazonensis*.

TABLE V

| Compound | Route of administration | Weight of lesions (g) (mean ± standard deviation) | % reduction in the number of parasites in the lesion | Mean of the number of parasites in the lesion per gram |
|---|---|---|---|---|
| Controls without treatment | | 0.061 ± 0.038 | — | $2.5 \times 10^7$ |
| Meglumine antimonate | Subcutaneous | 0.012 ± 0.010 | −97% | $7.2 \times 10^5$ |
| E-1-(2-Quinolyl) butene (6) | Oral | 0.101 ± 0.100 | −73% | $6.9 \times 10^6$ |
| Methyl E-3-(2-quinolyl)-2-propenate (23) | Oral | 0.059 ± 0.010 | −88%** | $3.1 \times 10^6$ |

Student's Test:
*P = 0.02,
**P = 0.05 (versus untreated group)

b) Tests Carried on Laboratory Animals Infected with Visceral Leishmaniasis (*Leishmania infantum*):

1/Laboratory Animals and Parasites

The experimental animals are male or female approximately 6- to 8-week-old Balb/c mice weighing 18-24 g, raised in the animal house of the Instituto de Investigaciones en Ciencias de la Salud, Asuncion, Paraguay. The Balb/c mice were infected with *Leishmania infantum* parasites at the promastigote stage (reference: MHOM/FR/91/LEM2259V), a strain isolated from a patient carrying AIDS. This strain is maintained in Schneider's drosophila culture medium (Gibco, USA) supplemented with 20% of fetal calf serum. The infectious promastigotes are cultured for 7 days and then counted. Each mouse is then infected intravenously with 0.2 ml of culture medium containing $10^7$ promastigotes.

2/Treatment of Visceral Leishmaniasis

The infected mice are distributed randomly in several groups of 8 mice, and then treated, one week after parasite infection, in the following way:

Glucantime® is administered subcutaneously at 100 mg/kg/day or 28 mg of $Sb^v$/kg/day, at a rate of one daily injection for 10 days;

the quinolines are administered orally at 25 mg/kg/day for 10 days, divided up into two doses, in the morning and at midday.

The quinolines or the N-methylglucamine antimoniate (Glucantime®) are dissolved in a drop of Tween 80 to which a phosphate buffered saline (PBS) solution is added so as to obtain the desired concentration, and 50 µl of the solution obtained are administered. The untreated control mice are given 50 µl of a solution of Tween 80 with PBS.

3/Parameters Studied

Counting of amastigotes forms in the liver and spleen.

After the treatments have been stopped and the animals sacrificed, the viscera, liver and spleen are weighed and collected in a Petri dish. Each organ is mounted several times on a degreased glass slide which, fixed and stained by the May-Grünwald-Giemsa technique, makes it possible to determine the number of amastigote forms per 500 nucleated cells. Next, the organs are cut up into pieces and ground using a 10 ml Potter grinder with 5 ml of RPMI culture medium. The 5 ml of puree obtained are centrifuged twice. The layer containing the amastigotes is subjected to counting of the number of parasites using a Neubauer cell. Five counts are performed on each amastigote layer. The number of amastigote forms is determined using the Stauber formula which takes into account the weight of the organ recovered:

A/N×W×coefficient of the Neubauer cell

A=number of amastigotes, N=number of nuclei W=weight of the lesion

A Student's test (t-test) is used for the statistical analysis of all the data. The comparison is made between "control" groups with a "treatment" group per pair. A value of P<0.05 is considered to be statistically significant. The results are expressed in Table VI.

Table VI illustrates the effectiveness of 3-(2-quinolyl) propenal (9), of 1-(2-quinolyl)acetylene (1), of methyl E-3-(2-quinolyl)-2-propenoate (23) and of Glucantime on Balb/c mice (n=8) infected with *Leishmania infantum* infected with *Leishmania infantum*.

group, a heteroaryl group, or a heteroaryl group substituted with one or more hydroxyl groups; or else a $C_1$-$C_{15}$ alkyl or $C_2$-$C_7$ alkenyl group carrying at least one substituent chosen from oxygen, halogens, and hydroxyl, formyl, carboxyl, aryloxycarbonyl, $C_2$-$C_8$ alkyloxycarbonyl, $C_3$-$C_9$ alkenyloxycarbonyl, nitrile, amine, $C_1$-$C_7$ alkoxy, phenoxy, $C_3$-$C_6$ cycloalkyl, aryl, heteroaryl, heteroaryloxy, arylsulfone, $C_1$-$C_7$ alkylsulfone, $C_1$-$C_7$ thioalkyl and $C_1$-$C_7$ aminoalkyl groups; or else a $C_2$-$C_7$ alkynyl group carrying at least one substituent chosen from oxygen, halogens, and hydroxyl, formyl, carboxyl, aryloxycarbonyl, $C_2$-$C_8$ alkyloxycarbonyl, $C_3$-$C_9$ alkenyloxycarbonyl, nitrile, aryl, heteroaryl, arylsulfone, $C_1$-$C_7$ alkylsulfone, $C_1$-$C_7$ thioalkyl and $C_1$-$C_7$ aminoalkyl groups; or else a $C_2$-$C_{15}$ alkenyl or alkynyl group substituted with at least one $C_1$-$C_7$ trialkylsilyl group; while $R_2$, which may be in the 3-, 6- or 8-position of the quinoline ring, represents a hydrogen or halogen atom, a hydroxyl group, formyl group, carboxyl group, $C_1$-$C_7$ alkyl group, $C_1$-$C_7$ alkoxy group, amine group, $C_1$-$C_{10}$ alkylamide group, $C_2$-$C_7$

TABLE VI

| Treatment | Weight of the liver (g) | Number of parasites in the liver per gram | % reduction in the number of parasites in the liver | Weight of the spleen (g) | Number of parasites in the spleen per gram | % reduction in the number of parasites in the spleen |
|---|---|---|---|---|---|---|
| Without treatment | 0.93 | $4.5 \times 10^7$ | | 0.10 | $4.2 \times 10^6$ | |
| Glucantime | 1.10 | $1.6 \times 10^7$ a | −65.3 | 0.11 | $4.4 \times 10^6$ | +6.0 |
| 3-(2-Quinolyl)-propenal (9) | 0.93 | $3.8 \times 10^6$ a, e | −91.6 | 0.11 | $2.2 \times 10^6$ b | −47.6 |
| 1-(2-Quinolyl)-acetylene (1) | 0.97 | $1.8 \times 10^7$ c | −60.0 | 0.11 | $2.2 \times 10^6$ b | −47.6 |
| Methyl E-3-(2-quinolyl-2-propenoate (23) | 1.01 | $1.8 \times 10^7$ d | −60.0 | 0.10 | $1.5 \times 10^6$ c, f | −64.3 |

Student's Test:
a p = 0.02 (versus group infected without treatment)
b p = 0.01 (versus group infected without treatment)
c p = 0.03 (versus group infected without treatment)
d p = 0.04 (versus group infected without treatment)
e p = 0.002 (versus group treated with Glucantime)
f p = 0.03 (versus group treated with Glucantime)

The invention claimed is:

1. A method for treating protozoan and retrovirus co-infections in an individual which comprises administering to said individual at least one quinoline corresponding to general formula (I):

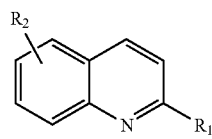

(I)

in which:
$R_1$ represents:
a hydrogen atom, a $C_1$-$C_{15}$ alkyl group, a $C_2$-$C_{15}$ alkenyl group, a $C_2$-$C_{15}$ alkynyl group, a formyl alkenyl group, a $C_2$-$C_7$ alkenyl group substituted with one or more $C_1$-$C_7$ alkoxy groups, a $C_2$-$C_{10}$ alkynyl group, or a $C_2$-$C_{10}$ alkynyl group substituted with a heteroaryl group;

or one of its pharmaceutically acceptable salts, on the condition, however, that $R_1$ and $R_2$ are not both a hydrogen atom, in a pharmaceutically acceptable carrier.

2. The method as claimed in claim 1, in which $R_1$ is different than a hydrogen atom.

3. The method as claimed in claim 1, in which:
$R_1$ represents:
a $C_2$-$C_{15}$ alkenyl or alkynyl group; or else
a $C_2$-$C_7$ alkenyl group carrying at least one substituent chosen from oxygen, halogens, and hydroxyl, formyl, carboxyl, $C_2$-$C_8$ alkyloxycarbonyl, nitrile, amine, $C_1$-$C_7$ alkoxy, phenoxy, $C_3$-$C_6$ cycloalkyl, aryl, heteroaryl, heteroaryloxy, arylsulfone, $C_1$-$C_7$ alkylsulfone, $C_1$-$C_7$ thioalkyl, $C_1$-$C_7$ aminoalkyl and trimethylsilyl, groups; or else a $C_2$-$C_7$ alkynyl group carrying at least one substituent chosen from oxygen, halogens, and hydroxyl, formyl, carboxyl, $C_2$-$C_8$ alkyloxycarbonyl, nitrile, aryl, heteroaryl, aryl-sulfone, $C_1$-$C_7$ alkylsulfone, $C_1$-$C_7$ thioalkyl, $C_1$-$C_7$ aminoalkyl and trimethylsilyl, groups; while $R_2$ represents a hydrogen atom, a hydroxyl group or a $C_1$-$C_7$ alkyl group.

4. The method as claimed in claim 1, in which $R_1$ represents a $C_2$-$C_7$ alkenyl or alkynyl group substituted with one or more halogen atoms.

5. The method as claimed in claim 1, for treating a co-infection induced by one or more protozoa belonging to the *Leishmania, Trypanosoma, Plasmodium, Toxoplasma, Pneumocystis* or *Schistosomia* genera and by a retrovirus of the HIV or HTLV-1 type.

6. The method as claimed in claim 5, for treating a *Leishmania*/HIV co-infection.

7. A quinoline corresponding to general formula (I):

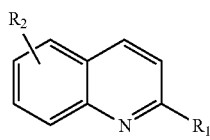

(I)

in which:
  either $R_1$ represents a $C_1$-$C_7$ alkyl group, a $C_2$-$C_7$ alkenyl group, or a $C_2$-$C_7$ alkenyl group carrying at least one substituent chosen from aryl groups, in which case $R_2$, which may be in the 3-, 6- or 8-position of the quinoline ring, represents a C3-C7 alkenyl group substituted with one or more C1-C7 alkoxy groups, or a C2-C10 alkynyl group substituted with a heteroaryl group;
  or $R_1$ represents a $C_1$-$C_7$ alkyl group carrying at least one substituent chosen from hydroxyl, amine, $C_1$-$C_4$ alkoxy and $C_1$-$C_4$ aminoalkyl groups, or $R_1$ represents a $C_2$-$C_7$ alkenyl group carrying at least one substituent chosen from hydroxyl, amine, $C_1$-$C_4$ alkoxy and $C_1$-$C_4$ aminoalkyl groups, in which case $R_2$, which may be in the 3-, 6- or 8-position of the quinoline ring, represents a $C_3$-$C_7$ alkenyl group substituted with one or more $C_1$-$C_7$ alkoxy groups, or a $C_2$-$C_{10}$ alkynyl group, or a $C_2$-$C_{10}$ alkynyl group substituted with a heteroaryl group;
  or $R_1$ represents:
  a methyl or ethyl group carrying at least one substituent chosen from halogens;
    in which case $R_2$, which may be in the 3-, 6- or 8-position of the quinoline ring, represents a $C_1$-$C_7$ alkoxy group, amine group, $C_1$-$C_{10}$ alkylamide group or $C_2$-$C_7$ alkenyl group substituted with one or more $C_1$-$C_7$ alkoxy groups, or else a $C_2$-$C_{10}$ alkynyl group substituted with a heteroaryl group;
  or $R_1$ represents:
  a 2-pyridyl radical
    in which case $R_2$, which may be in the 3-, 6- or 8-position of the quinoline ring, represents a hydrogen or halogen atom, formyl, carboxyl, $C_1$-$C_7$ alkyl, $C_1$-$C_7$ alkoxy, amine, $C_1$-$C_{10}$ alkylamide, $C_2$-$C_7$ alkeny, a $C_2$-$C_7$ alkenyl substituted with one or more $C_1$-$C_7$ alkoxy groups, a $C_2$-$C_{10}$ alkynyl group, a $C_2$-$C_{10}$ alkynyl group substituted with a heteroaryl group:

or $R_1$ represents:
a $C_8$-$C_{15}$ alkyl group, $C_8$-$C_{15}$ alkyl group carrying a substituent chosen from aryl groups; or else
a $C_8$-$C_{15}$ alkenyl group, a $C_2$-$C_7$ alkenyl group carrying at least one substituent chosen from arylsulfones; or else
a $C_2$-$C_{15}$ alkynyl group, a $C_2$-$C_7$ alkynyl group carrying at least one substituent chosen from aryl and arylsulfone groups;
  in which case $R_2$, which may be in the 3-, 6- or 8-position of the quinoline ring, represents a group chosen from a $C_1$-$C_7$ alkoxy, an amine, a $C_1$-$C_{10}$ alkylamide, a $C_2$-$C_7$ alkeny, a$C_2$-$C_7$ alkenyl substituted with one or more $C_1$-$C_7$ alkoxy groups, or else a $C_2$-$C_{10}$ alkynyl group substituted with a heteroaryl group;

or $R_1$ represents:
a formyl group. a heteroaryl group, a heteroaryl group substituted with one or more hydroxyl groups, with the exception of the 2-pyridyl radical; or else
a $C_1$-$C_{15}$ alkyl group carrying at least one substituent chosen from oxygen and formyl, carboxyl, aryloxycarbonyl, $C_2$-$C_8$ alkyloxycarbonyl, $C_3$-$C_9$ alkenyloxycarbonyl, nitrile, phenoxy, $C_3$-$C_6$ cycloalkyl, heteroaryloxy, arylsulfone, $C_1$-$C_7$ alkylsulfone and $C_1$-$C_7$ thioalkyl groups, a $C_1$-$C_7$ alkyl group carrying at least one substituent chosen from $C_5$-$C_7$ alkoxy and $C_5$-$C_7$ aminoalkyl groups, a $C_3$-$C_{15}$ alkyl group carrying at least one substituent chosen from halogens, a $C_6$-$C_{15}$ alkyl group substituted with at least one heteroaryl group, a $C_8$-$C_{15}$ alkyl group carrying at least one substituent chosen from hydroxyl, amine, $C_1$-$C_7$ alkoxy and $C_1$-$C_7$ aminoalkyl groups; or else
a $C_2$-$C_7$ alkenyl group carrying at least one substituent chosen from oxygen, halogens and carboxyl, aryloxycarbonyl, $C_2$-$C_8$ alkyloxycarbonyl, $C_3$-$C_9$ alkenyloxycarbonyl, nitrile, phenoxy, $C_3$-$C_6$ cycloalkyl, heteroaryloxy, $C_1$-$C_7$ alkylsulfone, $C_1$-$C_7$ thioalkyl, $C_1$-$C_7$ alkoxy and $C_5$-$C_7$ aminoalkyl groups; a $C_3$-$C_7$ alkenyl group substituted with a heteroaryl group; or else
a $C_2$-$C_7$ alkynyl group carrying at least one substituent chosen from oxygen, halogens and hydroxyl, formyl, carboxyl, aryloxycarbonyl, $C_2$-$C_8$ alkyloxycarbonyl, $C_3$-$C_9$ alkenyloxycarbonyl, nitrile, heteroaryl, $C_1$-$C_7$ alkylsulfone, $C_1$-$C_7$ thioalkyl and $C_1$-$C_7$ aminoalkyl groups; or else
a $C_2$-$C_{15}$ alkenyl or alkynyl group substituted with at least one $C_1$-$C_7$ trialkylsilyl group;
  in which case $R_2$, which may be in the 3-, 6- or 8-position of the quinoline ring, represents a hydrogen or halogen atom, a hydroxyl group, a formyl group, a carboxyl group, a $C_1$-$C_7$ alkyl group, a $C_1$-$C_7$ alkoxy group, an amine group, a $C_1$-$C_{10}$ alkylamide group or a $C_{2/}$-$C_7$ alkenyl group, a $C_2$-$C_{10}$ alkenyl group substituted with one or more $C_1$-$C_7$ alkoxy groups, or else a $C_2$-$C_{10}$ alkynyl group, a $C_2$-$C_{10}$ alkynyl group substituted with a heteroaryl group;
or one of its pharmaceutically acceptable salts.

8. A quinoline as claimed in claim 7, characterized in that:
either $R_1$ represents:
  a $C_2$-$C_7$ alkenyl group, a $C_2$-$C_7$ alkenyl group substituted with one or more groups chosen from hydroxyl, amine, aryl, $C_1$-$C_4$ alkoxy and $C_1$-$C_4$ aminoalkyl groups, in which case $R_2$ represents a group selected from: a $C_3$-$C_7$ alkenyl group substituted with one or more $C_1$-$C_7$ alkoxy groups, and a $C_2$-$C_{10}$ alkynyl group, a $C_2$-$C_{10}$ alkynyl group substituted with a heteroaryl group;

or $R_1$ represents:

a $C_2$-$C_7$ alkenyl group carrying at least one substituent chosen from oxygen, halogens and carboxyl, $C_2$-$C_8$ alkyloxycarbonyl, nitrile, phenoxy, $C_3$-$C_6$ cycloalkyl, heteroaryloxy, $C_1$-$C_7$ alkylsulfone, $C_1$-$C_7$ thioalkyl, $C_5$-$C_7$ alkoxy and $C_5$-$C_7$ aminoalkyl groups; a $C_3$-$C_7$ alkenyl group substituted with a heteroaryl group; or else a $C_2$-$C_7$ alkynyl group carrying at least one substituent chosen from oxygen, halogens and hydroxyl, carboxyl, $C_2$-$C_8$ alkyloxycarbonyl, nitrile, heteroaryl, $C_1$-$C_7$ alkylsulfone, $C_1$-$C_7$ thioalkyl and $C_1$-$C_7$ aminoalkyl groups; or else a $C_2$-$C_{15}$ alkenyl or alkynyl group substituted with at least one $C_1$-$C_7$ trialkylsilyl group;

in which case $R_2$ represents a hydrogen atom, a hydroxyl group or a $C_1$-$C_7$ alkyl group.

9. A quinoline as claimed in claim 7, characterized in that $R_1$ represents a $C_2$-$C_7$ alkenyl or alkynyl group substituted with one more halogen atoms.

10. A quinoline to general formula (I):

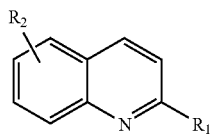

in which:

either $R_1$ represents a cyclopropyihydroxymethyl, 4-chlorobut-3-en-1-yn-1-yl, hept-1-en-1-yl, 2-bromoethenyl, 2-bromoethynyl, 2-bromo-2-fluoroethenyl, 4-methyl carboxylate buta-1,3-dien-1-yl, dec-1-yn-1-yl, 2-(2-quinoleyl)ethenyl or 2-(trimethylsilylethynyl)-4-trimethylsilylbut-1-en-3-yn-1-yl group, in which case $R_2$ represents a hydrogen atom;

or $R_1$ represents a prop-1-en-1-yl group, in which case $R_2$ represents a methyl group in the 6-position or a hydroxyl group in the 8-position of the quinoline ring;

or $R_1$ represents a 2-hydroxypropyl group, in which case $R_2$ represents a hydroxyl group in the 8-position of the quinoline ring;

or else $R_1$ represents a 2-methyl carboxylate ethenyl group, in which case $R_2$ represents a methyl group in the 6-position of the quinoline ring.

11. A pharmaceutical composition that comprises, as active principle, at least one quinoline as claimed in claim 10.

12. A pharmaceutical composition that comprises, as active principle, at least one quinoline as claimed in claim 8.

13. A pharmaceutical composition that comprises at least one quinoline according to claim 1 in a pharmaceutically acceptable carrier.

14. A method for the treatment of protozoan and retrovirus co-infections which comprises administering to a host having said co-infection a pharmaceutical composition containing at least one quinoline as claimed in claim 10.

15. A method for the treatment of protozoan and retrovirus co-infections which comprises administering to a host having said co-infection a pharmaceutical composition containing at least one quinoline as claimed in claim 8.

16. A method for the treatment of protozoan and retrovirus co-infections which comprises administering to a host having said co-infection at least one quinoline according to claim 1, in a pharmaceutically acceptable carrier.

* * * * *